US012360193B2

(12) United States Patent
Lin et al.

(10) Patent No.: US 12,360,193 B2
(45) Date of Patent: Jul. 15, 2025

(54) MODULARIZED MULTI-PURPOSE MAGNETIC RESONANCE PHANTOM

(71) Applicant: neuro42, Inc., San Francisco, CA (US)

(72) Inventors: Hung-Yu Lin, Walnut Creek, CA (US); Donghui Yin, San Francisco, CA (US); Nguyen Pham, San Francisco, CA (US); Sree Poojitha Yerramsetti, San Francisco, CA (US); Randy Link, El Cerrito, CA (US); Nio Anderson, San Francisco, CA (US); Rishabh Ostawal, San Francisco, CA (US); Joyce Ye, San Francisco, CA (US); Guanhao Fu, Richmond, CA (US); Ghoncheh Amouzandeh, Alameda, CA (US); Xiaowei Zou, San Francisco, CA (US)

(73) Assignee: neuro42, Inc., San Francisco, CA (US)

( * ) Notice: Subject to any disclaimer, the term of this patent is extended or adjusted under 35 U.S.C. 154(b) by 0 days.

(21) Appl. No.: 18/147,418

(22) Filed: Dec. 28, 2022

(65) Prior Publication Data
US 2024/0219504 A1     Jul. 4, 2024

(51) Int. Cl.
G01V 3/00     (2006.01)
G01R 33/56    (2006.01)
G01R 33/58    (2006.01)
A61B 5/055    (2006.01)

(52) U.S. Cl.
CPC ......... *G01R 33/58* (2013.01); *G01R 33/5608* (2013.01); *A61B 5/055* (2013.01)

(58) Field of Classification Search
CPC .............. G01R 33/3415; G01R 33/543; G01R 33/5659; G01R 33/36; A61B 5/055

USPC ........................................................ 324/309
See application file for complete search history.

(56) References Cited

U.S. PATENT DOCUMENTS

| 6,965,235 B1 | 11/2005 | Guclu et al. |
| 2010/0021029 A1 | 1/2010 | Pearlstein et al. |
| 2015/0084625 A1 | 3/2015 | Yin et al. |
| 2016/0155364 A1 | 6/2016 | Piron et al. |

(Continued)

FOREIGN PATENT DOCUMENTS

| CN | 1870761 B | * | 8/2011 | ........... H05K 5/0021 |
| CN | 203365664 U | | 12/2013 | |

(Continued)

OTHER PUBLICATIONS

International Search Report and Opinion for corresponding International Application No. PCT/US2023/085048, dated Mar. 12, 2024.

*Primary Examiner* — Walter L Lindsay, Jr.
*Assistant Examiner* — Frederick Wenderoth
(74) *Attorney, Agent, or Firm* — Wilson Sonsini Goodrich & Rosati

(57) ABSTRACT

The present disclosure provides magnetic resonance phantom imaging phantoms and method of assembling thereof. In one aspect, a magnetic resonance imaging phantom can include a plurality of modular components. The plurality of modular components can include a first modular component, a second modular component, a shell, and a lid. The second modular component can be different than the first modular component. The shell can be structured to receive at least one modular component. The lid can be attachable to the shell to enclose the at least one modular component received within the shell.

17 Claims, 10 Drawing Sheets

(56) References Cited

U.S. PATENT DOCUMENTS

| | | |
|---|---|---|
| 2016/0256711 A1 | 9/2016 | Pappas et al. |
| 2017/0169734 A1 | 6/2017 | Wen et al. |
| 2022/0291315 A1 | 9/2022 | Destrieux et al. |

FOREIGN PATENT DOCUMENTS

| | | | | |
|---|---|---|---|---|
| CN | 111226140 A | * | 6/2020 | ............ G01T 1/243 |
| WO | 2009105703 A1 | | 8/2009 | |
| WO | WO-2015003271 A1 | * | 1/2015 | ......... B29C 33/3835 |
| WO | 2022077125 A1 | | 4/2022 | |

* cited by examiner

MODULARIZED MULTI-PURPOSE MAGNETIC RESONANCE PHANTOM

BACKGROUND

The present disclosure relates to magnetic resonance imaging (MRI), medical imaging, medical intervention, and surgical intervention. MRI systems often include large and complex machines that generate significantly high magnetic fields and create significant constraints on the feasibility of certain surgical interventions. Restrictions can include limited physical access to the patient by a surgeon and/or a surgical robot and/or limitations on the usage of certain electrical and mechanical components in the vicinity of the MRI scanner. Such limitations are inherent in the underlying design of many existing systems and are difficult to overcome.

SUMMARY

In one aspect, the present disclosure describes a magnetic resonance imaging phantom kit. The magnetic resonance imaging phantom kit can include a plurality of modular components. The plurality of modular components can include a first modular component, a second modular component, a shell, and a lid. The second modular component can be different than the first modular component. The shell can be structured to receive at least one modular component. The lid can be attachable to the shell to enclose the at least one modular component received within the shell.

In another aspect, the present disclosure describes a method of assembling a magnetic resonance imaging phantom. The method can include selecting at least two components from a kit for a first calibration, assembling the at least two components to form a first configuration of the magnetic resonance imaging phantom, and performing the first calibration with the first configuration of the magnetic resonance imaging phantom. The method can further include disassembling the first configuration of magnetic resonance imaging phantom, selecting at least two modular components from the kit for a second calibration, assembling the at least two modular components to form a second configuration of the magnetic resonance imaging phantom, and performing the second calibration with the magnetic resonance imaging phantom. In some instances, the second configuration is different than the first configuration.

In yet another aspect, the present disclosure describes a magnetic resonance imaging phantom kit. The magnetic resonance imaging phantom kit can include a shell, a first modular component, and a second modular component. The shell can include shell interlocking features. The first modular component can include first interlocking features configured to interlock with the shell interlocking features in different configurations. The second modular component can be different than the first modular component. The second modular component can include second interlocking features configured to interlock with the shell interlocking features in different configurations. At least one of the first modular component and the second modular component can include a contrast insert configured to receive a contrast medium.

BRIEF DESCRIPTION OF THE DRAWINGS

The various aspects described herein, both as to organization and methods of operation, together with further objects and advantages thereof, may best be understood by reference to the following description, taken in conjunction with the accompanying drawings as follows.

Corresponding reference characters indicate corresponding parts throughout the several views. The exemplifications set out herein illustrate various disclosed embodiments, is one form, and such exemplifications are not to be construed as limiting the scope thereof in any manner.

DETAILED DESCRIPTION

Applicant of the present application also owns the following patent applications that were filed on even date herewith and which are each herein incorporated by reference in their respective entireties:

U.S. patent application Ser. No. 18/147,542, titled INTRACRANIAL RADIO FREQUENCY COIL FOR INTRAOPERATIVE MAGNETIC RESONANCE IMAGING.

U.S. patent application Ser. No. 18/147,556, titled DEEP LEARNING SUPER-RESOLUTION TRAINING FOR ULTRA LOW-FIELD MAGNETIC RESONANCE IMAGING.

Applicant of the present application also owns the following patent applications, which are each herein incorporated by reference in their respective entireties:

International Patent Application No. PCT/US2022/72143, titled NEURAL INTERVENTIONAL MAGNETIC RESONANCE IMAGING APPARATUS, filed May 5, 2022.

U.S. patent application Ser. No. 18/057,207, titled SYSTEM AND METHOD FOR REMOVING ELECTROMAGNETIC INTERFERENCE FROM LOW-FIELD MAGNETIC RESONANCE IMAGES, filed Nov. 19, 2022.

Before explaining various aspects of interventional magnetic resonance imaging devices in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to neural interventional magnetic resonance imaging (MRI) devices that allows for the integration of surgical intervention and guidance with an MRI. This includes granting physical access to the area around the patient as well as access to the patient's head with one or more access apertures. In addition, the neural interventional MRI device may allow for the usage of robotic guidance tools and/or traditional surgical implements. In various instances, a neural interventional MRI can be used intraoperatively to obtain scans of a patient's head and/or brain during a surgical intervention, such as a surgical procedure like a brain biopsy or neurosurgery.

Figure 1:
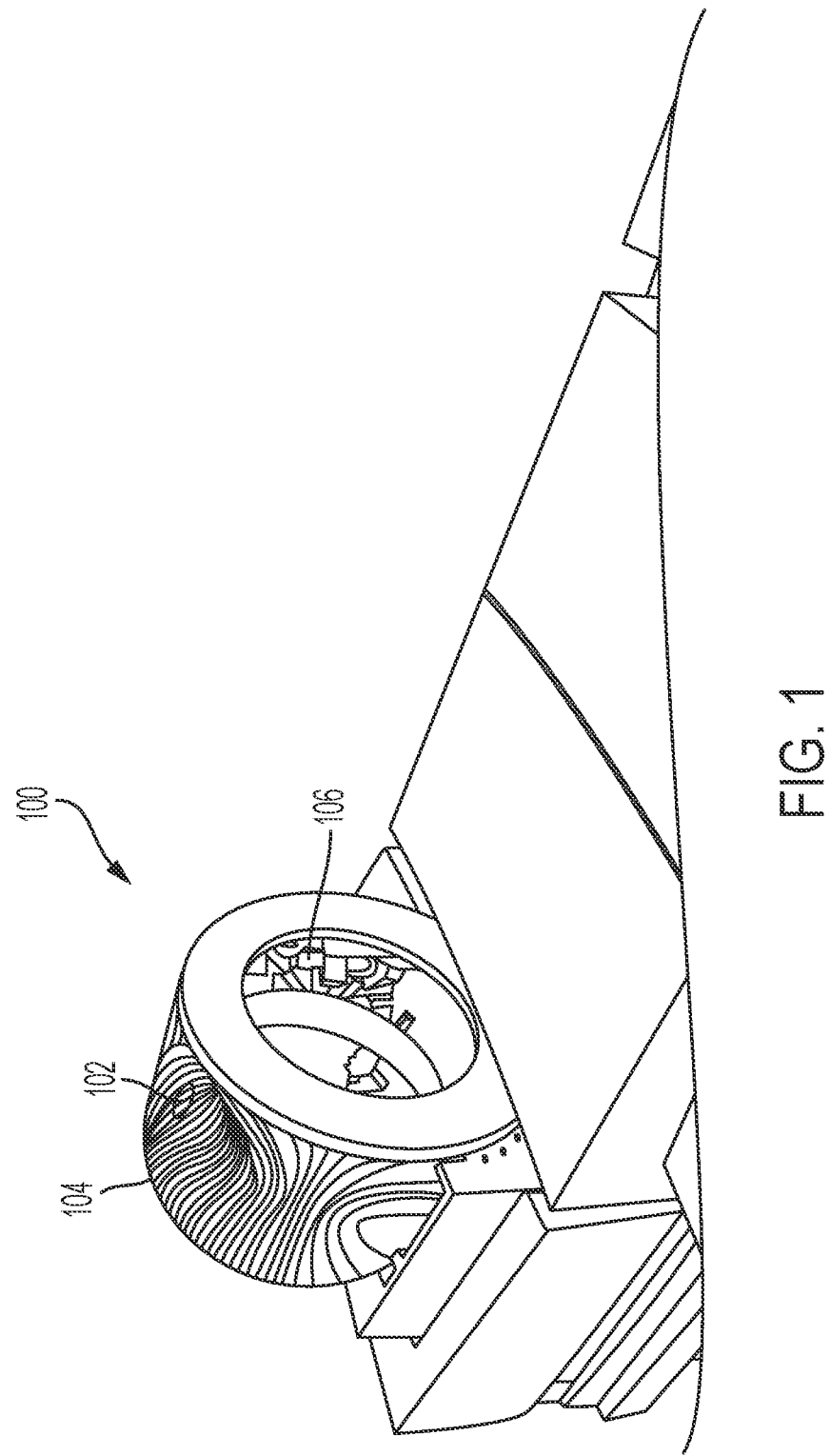
FIG. 1 depicts components of a MRI scanning system including a dome-shaped housing for a magnetic array, the dome-shaped housing surrounding a region of interest therein and further depicting the dome-shaped housing positioned to receive at least a portion of the head of a patient reclined on the table into the region of interest, in accordance with at least one aspect of the present disclosure.

FIG. 1 depicts a MRI scanning system 100 that includes a dome-shaped housing 102 configured to receive a patient's head. The dome-shaped housing 102 can further include at least one access aperture configured to allow access to the patient's head to enable a neural intervention. A space within the dome-shaped housing 102 forms the region of interest for the MRI scanning system 100. Target tissue in the region of interest is subjected to magnetization fields/pulses, as further described herein, to obtain imaging data representative of the target tissue.

Figure 1A:
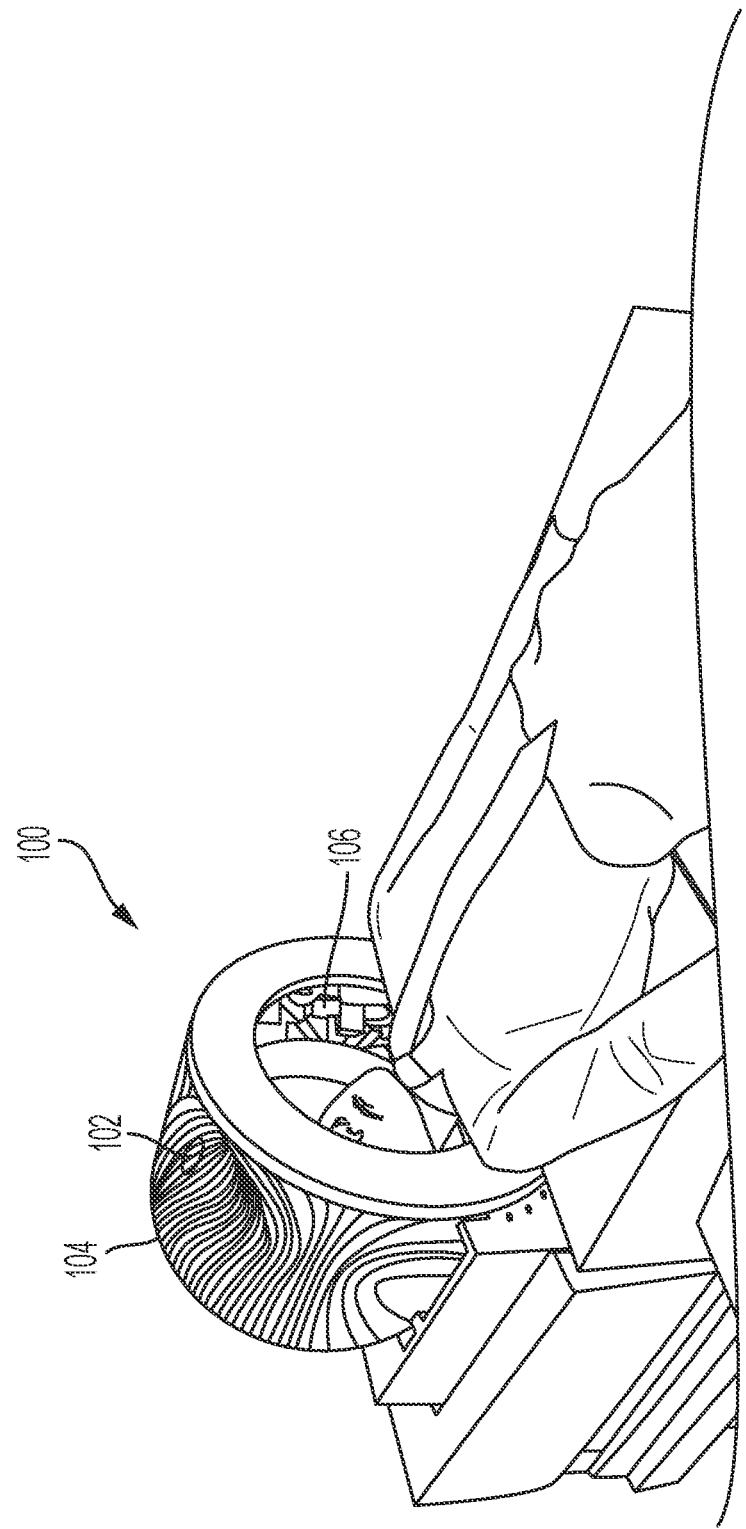
FIG. 1A depicts a patient's head positioned in the region of interest of the MRI scanning system of FIG. 1.

For example, referring to FIG. 1A, a patient can be positioned such that his/her head is positioned within the region of interest within the dome-shaped housing 102. The brain can be positioned entirely within the dome-shaped housing 102. In such instances, to facilitate intracranial interventions (e.g. neurosurgery) in concert with MR imaging, the dome-shaped housing 102 can include one or more apertures that provide access to the brain. Apertures can be spaced apart around the perimeter of the dome-shaped housing.

The MRI scanning system 100 can include an auxiliary cart (see, e.g. auxiliary cart 540 in FIG. 6) that houses certain conventional MRI electrical and electronic components, such as a computer, programmable logic controller, power distribution unit, and amplifiers, for example. The MRI scanning system 100 can also include a magnet cart that holds the dome-shaped housing 102, gradient coil(s), and/or a transmission coil, as further described herein. Additionally, the magnet cart can be attached to a receive coil in various instances. Referring primarily to FIG. 1, the dome-shaped housing 102 can further include RF transmission coils, gradient coils 104 (depicted on the exterior thereof), and shim magnets 106 (depicted on the interior thereof). Alternative configurations for the gradient coil(s) 104 and/or shim magnets 106 are also contemplated. In various instances, the shim magnets 106 can be adjustably positioned in a shim tray within the dome-shaped housing 102, which can allow a technician to granularly configure the magnetic flux density of the dome-shaped housing 102.

Various structural housings for receiving the patient's head and enabling neural interventions can be utilized with a MRI scanning system, such as the MRI scanning system 100. In one aspect, the MRI scanning system 100 may be outfitted with an alternative housing, such as a dome-shaped housing 202 (FIG. 2) or a two-part housing 302 (FIG. 3) configured to form a dome-shape. The dome-shaped housing 202 defines a plurality of access apertures 203; the two-part housing 302 also defines a plurality of access apertures 303 and further includes an adjustable gap 305 between the two parts of the housing.

Figure 3:
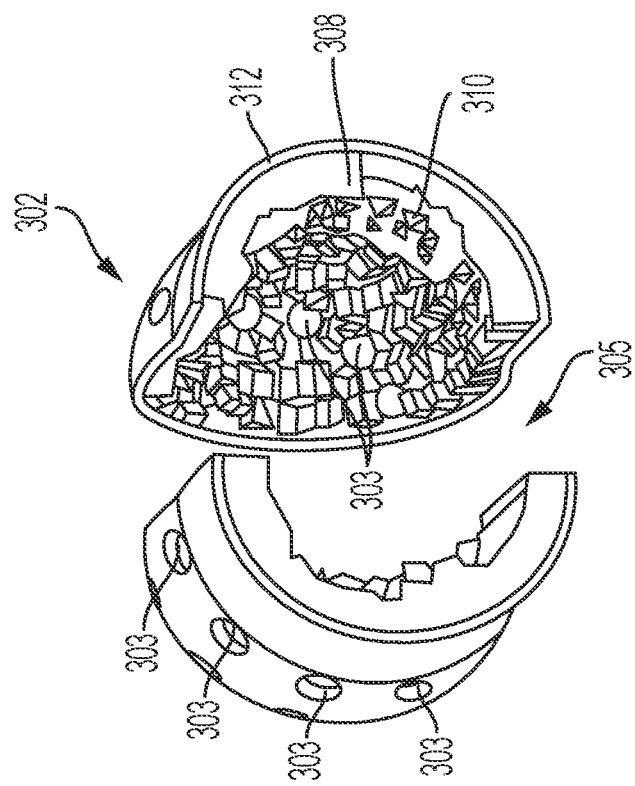
FIG. 3 is a perspective view of an alternative dome-shaped housing for a magnetic array for use with the MRI scanning system of FIG. 1, wherein access apertures and an adjustable gap is defined in the dome-shaped housing, in accordance with at least one aspect of the present disclosure.

In various instances, the housings 202 and 302 can include a bonding agent 308, such as an epoxy resin, for example, that holds a plurality of magnetic elements 310 in fixed positions. The plurality of magnetic elements 310 can be bonded to a structural housing 312, such as a plastic substrate, for example. In various aspects, the bonding agent 308 and structural housing 312 may be non-conductive or diamagnetic materials. Referring primarily to FIG. 3, the two-part housing 302 comprises two structural housings 312. In various aspect, a structural housing for receiving the patient's head can be formed from more than two sub-parts. The access apertures 303 in the structural housing 312 provide a passage directly to the patient's head and are not obstructed by the structural housing 312, bonding agent 308, or magnetic elements 310. The access apertures 303 can be positioned in an open space of the housing 302, for example.

There are many possible configurations of neural interventional MRI devices that can achieve improved access for surgical intervention. Many configurations build upon two main designs, commonly known as the Halbach cylinder and the Halbach dome described in the following article: Cooley et al. (e.g. Cooley, C. Z., Haskell, M. W., Cauley, S. F., Sappo, C., Lapierre, C. D., Ha, C. G., Stockmann, J. P., & Wald, L. L. (2018). Design of sparse Halbach magnet arrays for portable MRI using a genetic algorithm. *IEEE transactions on magnetics,* 54(1), 5100112. The article "Design of sparse Halbach magnet arrays for portable MRI using a genetic algorithm" by Cooley et al., published in *IEEE transactions on magnetics,* 54(1), 5100112 in 2018, is incorporated by reference herein in its entirety.

In various instances, a dome-shaped housing for an MRI scanning system, such as the system 100, for example, can include a Halbach dome defining a dome shape and configured based on several factors including main magnetic field $B_0$ strength, field size, field homogeneity, device size, device weight, and access to the patient for neural intervention. In various aspects, the Halbach dome comprises an exterior radius and interior radius at the base of the dome. The Halbach dome may comprise an elongated cylindrical portion that extends from the base of the dome. In one aspect, the elongated cylindrical portion comprises the same exterior radius and interior radius as the base of the dome and continues from the base of the dome at a predetermined length, at a constant radius. In another aspect, the elongated cylindrical portion comprises a different exterior radius and interior radius than the base of the dome (see e.g. FIGS. 2 and 3). In such instances, the different exterior radius and interior radius of the elongated cylindrical portion can merge with the base radii in a transitional region.

Figure 2:
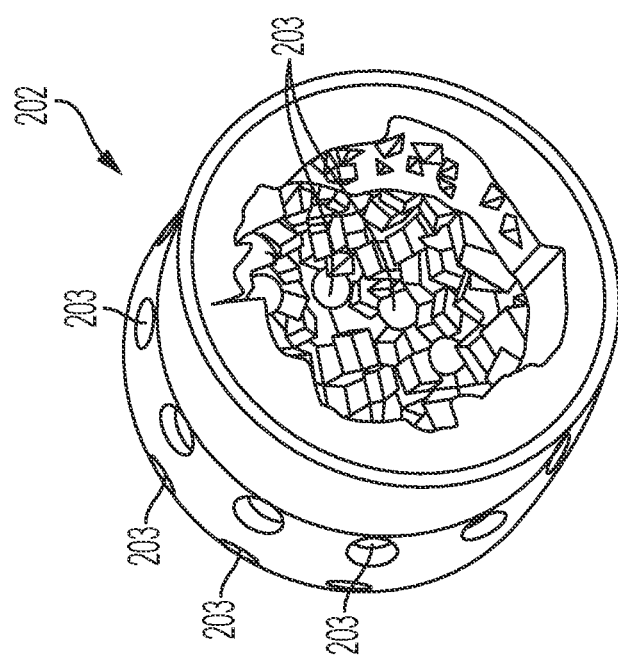
FIG. 2 is a perspective view of an alternative dome-shaped housing for a magnetic array for use with the MRI scanning system of FIG. 1, wherein access apertures are defined in the dome-shaped housing, in accordance with at least one aspect of the present disclosure.
Figure 4:
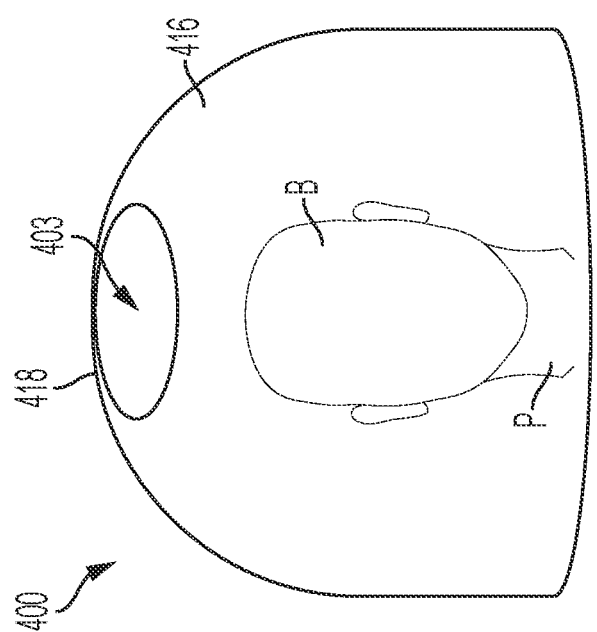
FIG. 4 depicts a dome-shaped housing for use with a MRI scanning system having an access aperture in the form of a centrally-defined hole, in accordance with at least one aspect of the present disclosure.

FIG. 4 illustrates an exemplary Halbach dome 400 for an MRI scanning system, such as the system 100, for example, which defines an access aperture in the form of a hole or access aperture 403, where the dome 400 is configured to receive a head and brain B of the patient P within the region of interest therein, and the access aperture 403 is configured to allow access to the patient P to enable neural intervention with a medical instrument and/or robotically-controlled surgical tool, in accordance with at least one aspect of the present disclosure. The Halbach dome 400 can be built with a single access aperture 403 at the top side 418 of the dome 400, which allows for access to the top of the skull while minimizing the impact to the magnetic field. Additionally or alternatively, the dome 300 can be configured with multiple access apertures around the structure 416 of the dome 400, as shown in FIGS. 2 and 3.

The diameter $D_{hole}$ of the access aperture 403 may be small (e.g. about 2.54 cm) or very large (substantially the exterior $r_{ext}$ diameter of the dome 400). As the access aperture 403 becomes larger, the dome 400 begins to resemble a Halbach cylinder, for example. The access aperture 403 is not limited to being at the apex of the dome 400. The access aperture 403 can be placed anywhere on the surface or structure 416 of the dome 400. In various instances, the entire dome 400 can be rotated so that the access aperture 403 can be co-located with a desired physical location on the patient P.

Figure 5:
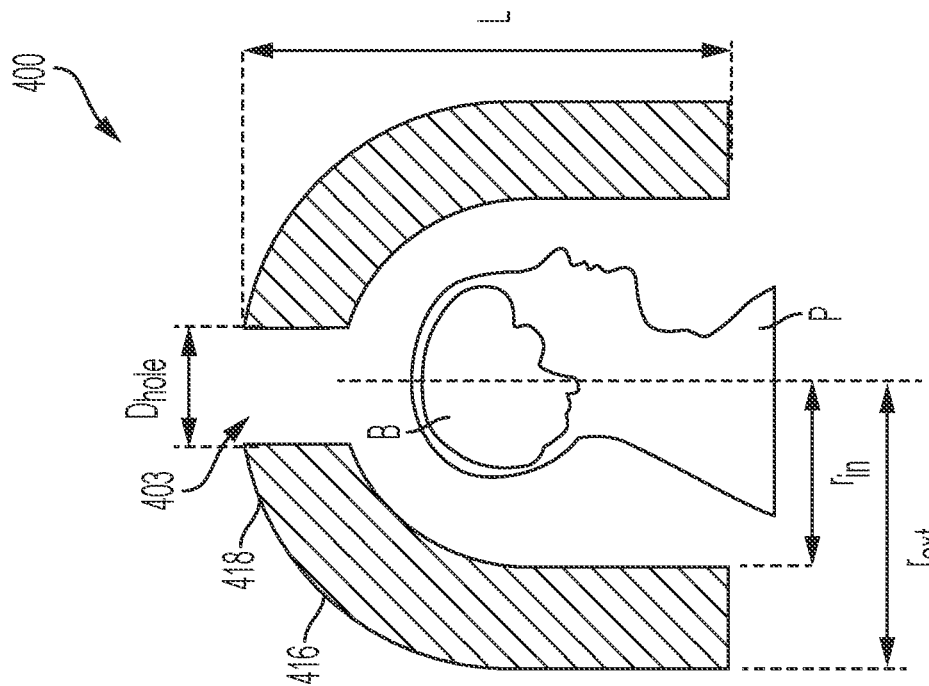
FIG. 5 is a cross-sectional view of the dome-shaped housing of FIG. 4, in accordance with at least one aspect of the present disclosure.

FIG. 5 depicts relative dimensions of the Halbach dome 400, including a diameter $D_{hole}$ of the access aperture 403, a length L of the dome 400, and an exterior radius Text and an interior radius $r_{in}$ of the dome 400. The Halbach dome 400 comprises a plurality of magnetic elements that are configured in a Halbach array and make up a magnetic assembly. The plurality of magnetic elements may be enclosed by the exterior radius text and interior radius $r_{in}$ in the structure 416 or housing thereof. In one aspect, example dimensions may be defined as: $r_{in}$=19.3 cm; $r_{ext}$=23.6 cm; L=38.7 cm; and 2.54 cm≤D<19.3 cm.

Based on the above example dimensions, a Halbach dome 400 with an access aperture 403 may be configured with a magnetic flux density $B_0$ of around 72 mT, and an overall mass of around 35 kg. It will be appreciated that the dimensions may be selected based on particular applications to achieve a desired magnetic flux density $B_0$, total weight of the Halbach dome 400 and/or magnet cart, and geometry of the neural intervention access aperture 403.

In various aspects, the Halbach dome 400 may be configured to define multiple access apertures 403 placed around the structure 416 of the dome 400. These multiple access apertures 403 may be configured to allow for access to the patient's head and brain B using tools (e.g., surgical tools) and/or a surgical robot.

In various aspects, the access aperture 403 may be adjustable. The adjustable configuration may provide the ability for the access aperture 403 to be adjusted using either a motor, mechanical assist, or a hand powered system with a mechanical iris configuration, for example, to adjust the diameter $D_{hole}$ of the access aperture 403. This would allow for configuration of the dome without an access aperture 403, conducting an imaging scan, and then adjusting the configuration of the dome 400 and mechanical iris thereof to include the access aperture 403 and, thus, to enable a surgical intervention therethrough.

Halbach domes and magnetic arrays thereof for facilitating neural interventions are further described in International Patent Application No. PCT/US2022/72143, titled NEURAL INTERVENTIONAL MAGNETIC RESONANCE IMAGING APPARATUS, filed May 5, 2022, which is incorporated by reference herein in its entirety.

Figure 6:
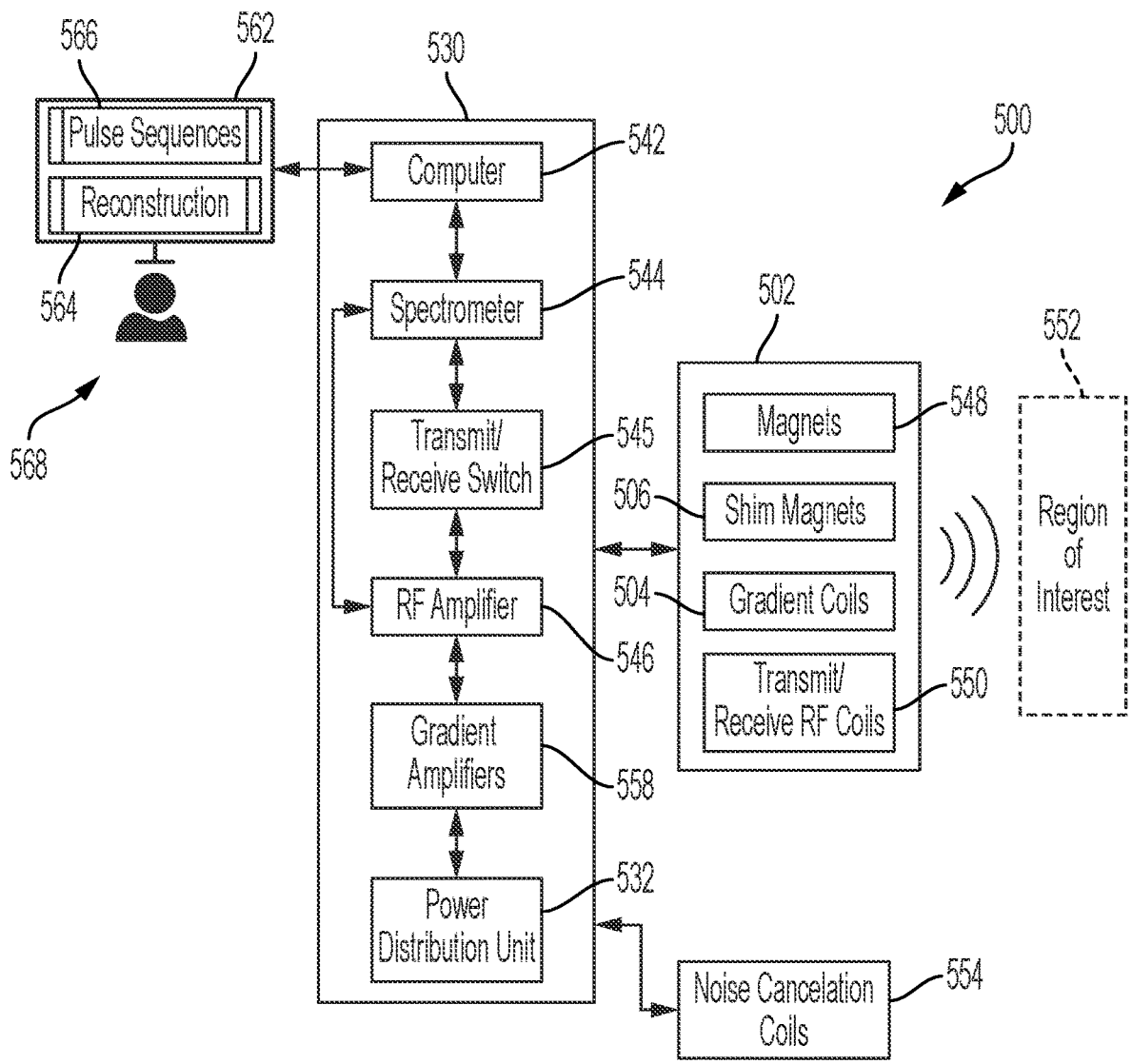
FIG. 6 depicts a control schematic for a MRI system, in accordance with at least one aspect of the present disclosure.

Referring now to FIG. 6, a schematic for an MRI system 500 is shown. The MRI scanning system 100 (FIG. 1) and the various dome-shaped housings and magnetic arrays therefor, which are further described herein, for example, can be incorporated into the MRI system 500, for example. The MRI system 500 includes a housing 502, which can be similar in many aspects to the dome-shaped housings 102 (FIG. 1), 202 (FIG. 2), and/or 302 (FIG. 3), for example. The housing 502 is dome-shaped and configured to form a region of interest, or field of view, 552 therein. For example, the housing 502 can be configured to receive a patient's head in various aspects of the present disclosure.

The housing 502 includes a magnet assembly 548 having a plurality of magnets arranged therein (e.g. a Halbach array of magnets). In various aspect, the main magnetic field $B_0$, generated by the magnetic assembly 548, extends into the field of view 552, which contains an object (e.g. the head of a patient) that is being imaged by the MRI system 500.

The MRI system 500 also includes RF transmit/receive coils 550. The RF transmit/receive coils 550 are combined into integrated transmission-reception (Tx/Rx) coils. In other instances, the RF transmission coil can be separate from the RF reception coil. For example, the RF transmission coil(s) can be incorporated into the housing 502 and the RF reception coil(s) can be positioned within the housing 502 to obtain imaging data.

The housing 502 also includes one or more gradient coils 504, which are configured to generate gradient fields to facilitate imaging of the object in the field of view 552 generated by the magnet assembly 548, e.g., enclosed by the dome-shaped housing and dome-shaped array of magnetic elements therein. Shim trays adapted to receive shim magnets 506 can also be incorporated into the housing 502.

During the imaging process, the main magnetic field $B_0$ extends into the field of view 552. The direction of the effective magnetic field ($B_1$) changes in response to the RF pulses and associated electromagnetic fields transmitted by the RF transmit/receive coils 550. For example, the RF transmit/receive coils 550 may be configured to selectively transmit RF signals or pulses to an object in the field of view 552, e.g. tissue of a patient's brain. These RF pulses may alter the effective magnetic field experienced by the spins in the sample tissue.

The housing 502 is in signal communication with an auxiliary cart 530, which is configured to provide power to the housing 502 and send/receive control signals to/from the housing 502. The auxiliary cart 530 includes a power distribution unit 532, a computer 542, a spectrometer 544, a transmit/receive switch 545, an RF amplifier 546, and gradient amplifiers 558. In various instances, the housing 502 can be in signal communication with multiple auxiliary carts and each cart can support one or more of the power distribution unit 532, the computer 542, the spectrometer 544, the transmit/receive switch 545, the RF amplifier 546, and/or the gradient amplifiers 558.

The computer 542 is in signal communication with a spectrometer 544 and is configured to send and receive signals between the computer 542 and the spectrometer 544. When the object in the field of view 552 is excited with RF pulses from the RF transmit/receive coils 550, the precession of the object results in an induced electric current, or MR current, which is detected by the RF transmit/receive coils 550 and sent to the RF preamplifier 556. The RF preamplifier 556 is configured to boost or amplify the excitation data signals and send them to the spectrometer 544. The spectrometer 544 is configured to send the excitation data to the computer 542 for storage, analysis, and image construction. The computer 542 is configured to combine multiple stored excitation data signals to create an image, for example. In various instances, the computer 542 is in signal communication with at least one database 562 that stores reconstruction algorithms 564 and/or pulse sequences 566. The computer 542 is configured to utilize the reconstruction algorithms to generate an MR image 568.

From the spectrometer 544, signals can also be relayed to the RF transmit/receive coils 550 in the housing 502 via an RF power amplifier 546 and the transmit/receive switch 545 positioned between the spectrometer 544 and the RF power amplifier 546. From the spectrometer 544, signals can also be relayed to the gradient coils 560 in the housing 502 via a gradient power amplifier 558. For example, the RF power amplifier 546 is configured to amplify the signal and send it to RF transmission coils 560, and the gradient power amplifier 558 is configured to amplify the gradient coil signal and send it to the gradient coils 560.

In various instances, the MRI system 500 can include noise cancellation coils 554. For example, the auxiliary cart 530 and/or computer 542 can be in signal communication with noise cancellation coils 554. In other instances, the noise cancellation coils 554 can be optional. For example, certain MRI systems disclosed herein may not include supplemental/auxiliary RF coils for detecting and canceling electromagnetic interference, i.e. noise.

Figure 7:
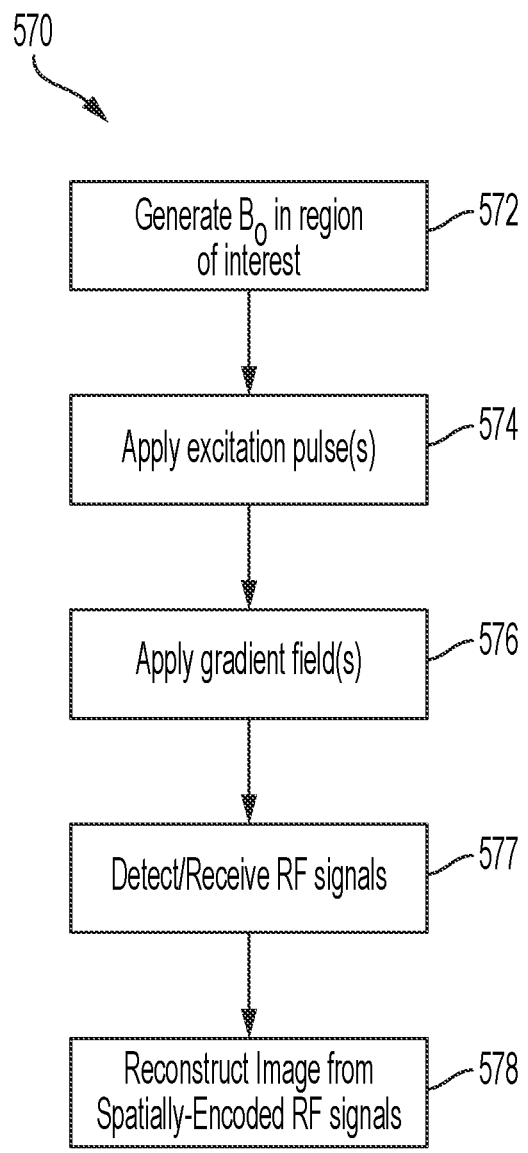
FIG. 7 is a flowchart describing a method for obtaining imaging data from an MRI system, in accordance with at least one aspect of the present disclosure.

A flowchart depicting a process 570 for obtaining an MRI image is shown in FIG. 7. The flowchart can be implemented by the MRI system 500, for example. In various instances, at block 572, the target subject (e.g. a portion of a patient's anatomy), is positioned in a main magnetic field $B_0$ in an interest of region (e.g. region of interest 552), such as within the dome-shaped housing of the various MRI scanners further described herein (e.g. magnet assembly 548). The main magnetic field $B_0$ is configured to magnetically polarize the hydrogen protons (1H-protons) of the target subject (e.g. all organs and tissues) and is known as the net longitudinal magnetization Mo. It is proportional to the proton density (PD) of the tissue and develops exponentially in time with a time constant known as the longitudinal relaxation time T1 of the tissue. T1 values of individual tissues depend on a number of factors including their microscopic structure, on the water and/or lipid content, and the strength of the polarizing magnetic field, for example. For these reasons, the T1 value of a given tissue sample is dependent on age and state of health.

At block 574, a time varying oscillatory magnetic field $B_1$, i.e. an excitation pulse, is applied to the magnetically polarized target subject with a RF coil (e.g. RF transmit/receive coil 550). The carrier frequency of the pulsed $B_1$ field is set to the resonance frequency of the 1H-proton, which causes the longitudinal magnetization to flip away from its equilibrium longitudinal direction resulting in a rotated magnetization vector, which in general can have transverse as well as longitudinal magnetization components, depending on the flip angle used. Common $B_1$ pulses include an inversion pulse, or a 180-degree pulse, and a 90-degree pulse. A 180-degree pulse reverses the direction of the 1H-proton's magnetization in the longitudinal axis. A 90-degree pulse rotates the 1H-proton's magnetization by 90 degrees so that the magnetization is in the transverse plane. The MR signals are proportional to the transverse components of the magnetization and are time varying electrical currents that are detected with suitable RF coils. These MR signals decay exponentially in time with a time constant known as the transverse relaxation time T2, which is also dependent on the microscopic tissue structure, water/lipid content, and the strength of the magnetic field used, for example.

At block 576, the MR signals are spatially encoded by exposing the target subject to additional magnetic fields generated by gradient coils (e.g. gradient coils 560), which are known as the gradient fields. The gradient fields, which vary linearly in space, are applied for short periods of time in pulsed form and with spatial variations in each direction. The net result is the generation of a plurality of spatially encoded MR signals, which are detected at block 577, and which can be reconstructed to form MR images depicting slices of the examination subject. A RF reception coil (e.g. RF transmit/receive coil 550) can be configured to detect the spatially-encoded RF signals. Slices may be oriented in the transverse, sagittal, coronal, or any oblique plane.

At block 578, the spatially encoded signals of each slice of the scanned region are digitized and spatially decoded mathematically with a computer reconstruction program (e.g. by computer 542) in order to generate images depicting the internal anatomy of the examination subject. In various instances, the reconstruction program can utilize an (inverse) Fourier transform to back-transforms the spatially-encoded data (k-space data) into geometrically decoded data.

Figure 8:
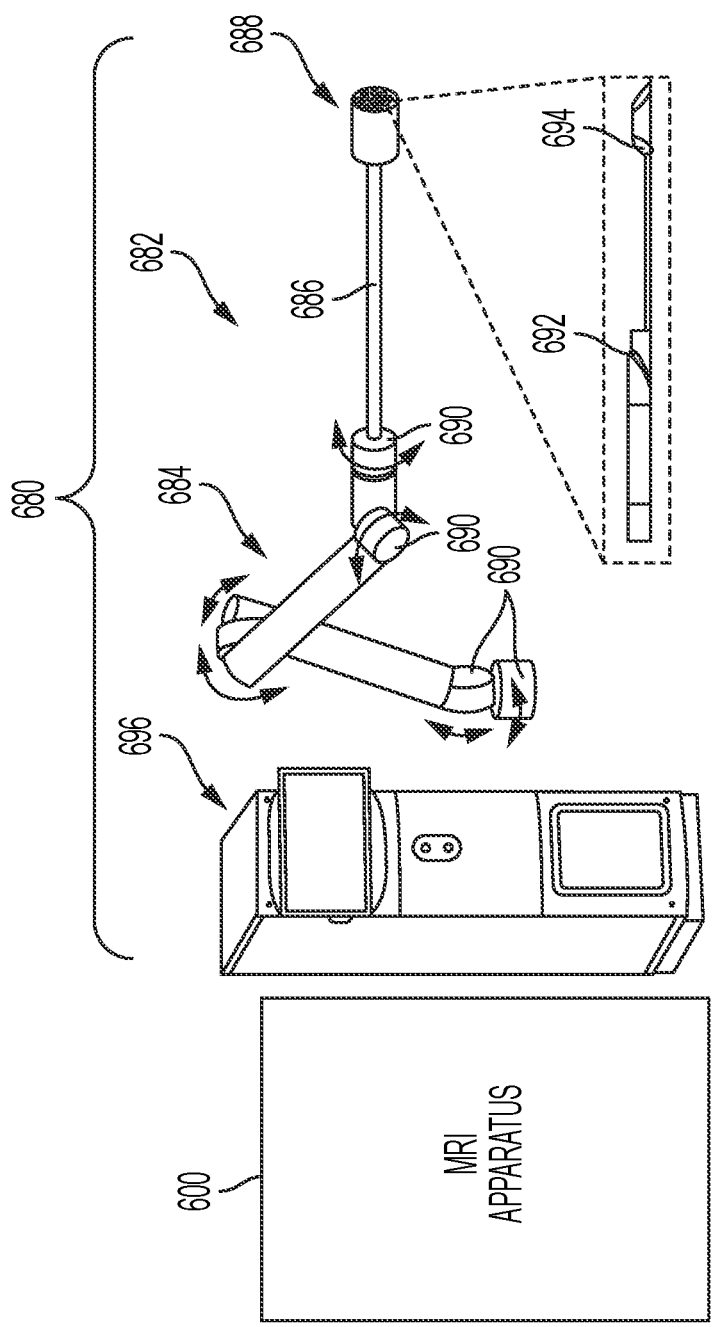
FIG. 8 depicts a MRI scanning system and a robotic system, in accordance with at least one aspect of the present disclosure.

FIG. 8 depicts a graphical illustration of a robotic system 680 that may be used for neural intervention with an MRI scanning system 600. The robotic system 680 includes a computer system 696 and a surgical robot 682. The MRI scanning system 600 can be similar to the MRI system 500 and can include the dome-shaped housing and magnetic arrays having access apertures, as further described herein. For example, the MRI system 500 can include one or more access apertures defined in a Halbach array of magnets in the permanent magnet assembly to provide access to one or more anatomical parts of a patient being imaged during a medical procedure. In various instances, a robotic arm and/or tool of the surgical robot 682 is configured to extend through an access aperture in the permanent magnet assembly to reach a patient or target site. Each access aperture can provide access to the patient and/or surgical site. For example, in instances of multiple access apertures, the multiple access apertures can allow access from different directions and/or proximal locations.

In accordance with various embodiments, the robotic system 680 is configured to be placed outside the MRI system 600. As shown in FIG. 8, the robotic system 680 can include a robotic arm 684 that is configured for movements with one or more degrees of freedom. In accordance with various embodiments, the robotic arm 684 includes one or more mechanical arm portions, including a hollow shaft 686 and an end effector 688. The hollow shaft 686 and end effector 688 are configured to be moved, rotated, and/or swiveled through various ranges of motion via one or more motion controllers 690. The double-headed curved arrows in FIG. 8 signify exemplary rotational motions produced by the motion controllers 690 at the various joints in the robotic arm 684.

In accordance with various embodiments, the robotic arm 684 of the robotic system 682 is configured for accessing various anatomical parts of interest through or around the MRI scanning system 600. In accordance with various embodiments, the access aperture is designed to account for the size of the robotic arm 684. For example, the access aperture defines a circumference that is configured to accommodate the robotic arm 684, the hollow shaft 686, and the end effector 688 therethrough. In various instances, the robotic arm 684 is configured for accessing various anatomical parts of the patient from around a side of the magnetic imaging apparatus 600. The hollow shaft 686 and/or end effector 688 can be adapted to receive a robotic tool 692, such as a biopsy needle having a cutting edge 694 for collecting a biopsy sample from a patient, for example.

The reader will appreciate that the robotic system 682 can be used in combination with various dome-shaped and/or cylindrical magnetic housings further described herein. Moreover, the robotic system 682 and robotic tool 692 in FIG. 8 are exemplary. Alternative robotic systems can be utilized in connection with the various MRI systems disclosed herein. Moreover, handheld surgical instruments and/or additional imaging devices (e.g. an endoscope) and/or systems can also be utilized in connection with the various MRI systems disclosed herein.

In various aspects of the present disclosure, the MRI systems described herein can comprise low field MRI (LF-MRI) systems. In such instances, the main magnetic field $B_0$ generated by the permanent magnet assembly can be between 0.1 T and 1.0 T, for example. In other instances, the MRI systems described herein can comprise ultra-low field MRI (ULF-MRI) systems. In such instances, the main magnetic field $B_0$ generated by the permanent magnet assembly can be between 0.03 T and 0.1 T, for example.

Higher magnetic fields, such as magnetic fields above 1.0 T, for example, can preclude the use of certain electrical and mechanical components in the vicinity of the MRI scanner. For example, the existence of surgical instruments and/or surgical robot components comprising metal, especially ferrous metals, can be dangerous in the vicinity of higher magnetic fields because such tools can be drawn toward the source of magnetization. Moreover, higher magnetic fields often require specifically-designed rooms with additional precautions and shielding to limit magnetic interference. Despite the limitations on high field MRI systems, low field and ultra-low field MRI systems present various challenges to the acquisition of high quality images with sufficient resolution for achieving the desired imaging objectives.

LF- and ULF-MRI systems generally define an overall magnetic field homogeneity that is relatively poor in comparison to higher field MRI systems. For example, a dome-shaped housing for an array of magnets, as further described herein, can comprise a Halbach array of permanent magnets, which generate a magnetic field $B_0$ having a homogeneity between 1,000 ppm and 10,000 ppm in the region of interest in various aspects of the present disclosure.

MRI phantoms are used to evaluate MRI performance based on known properties. For example, an MRI phantom can be used to characterize an MRI system to comply with design requirements. MRI phantoms can be used to characterize geometric distortion, contrast, structure, SNR, and/or intracranial vascular flow, for example. Additionally or alternatively, MRI phantoms can be used to track the performance of an MRI system over time and/or across multiple sites. Existing phantoms are generally designed for high-field systems, such as MRI systems utilizing a magnetic field strength greater than 1.0 T, greater than 1.5 T and/or between 1.5 T and 3.0 T, for example.

During design of MRI systems, such as LF- or ULF-MRI systems used in connection with neurological interventions, for example, a modularized multi-purpose phantom may be useful in certain instances to calibrate, test, evaluation, and/or optimize the system. For example, a magnetic resonance phantom kit having modular, interchangeable components and/or configurations can be used to calibrate, test, evaluate and/or optimize characteristics of the MRI systems for multiple iterations of the design. Characterizations can include brain tissue contrast of T1-weighted scans (T1w), T2-weighted (T2w), proton density-weighted (PD), and fluid-attenuated inversion recovery (FLAIR) imaging data. Additionally, it would be useful to evaluate diffusion-weighted (DWI) imaging data, in certain instances.

A MRI phantom kit can provide a modularized system for multi-purpose validation of various characteristics of the MRI system in certain instances.

In one aspect of the present disclosure, a MRI phantom kit can include a plurality of components including multiple modular and/or interchangeable components, such as a first modular component and a second modular component. The second modular component can be different than the first modular component. The plurality of components can further include a shell structured to receive at least one of the modular and/or interchangeable components and can also include a lid attachable to the shell to enclose the at least one modular and/or interchangeable components received within the shell.

Exemplary modular and/or interchangeable components include a grid insert, a contrast insert, and/or an anatomical model insert, for example. One or more of the inserts can be configured to receive a contrast medium, for example. In various instances, the inserts and/or the contrast mediums received in the insert(s) can be configured in different configurations, such as different layers of the assembled MRI phantom. Each layer can correspond to a different slice of an MRI image, for example.

In various instances, MRI phantoms assembled from a modularized and/or multi-purpose kit can be exchangeable, extendable, customizable and/or more cost effective than existing alternatives, especially during product development and design, for example. The kit can be reassembled with different components and/or in different configurations for alternative testing and/or calibration scans, for example.

Figure 9:
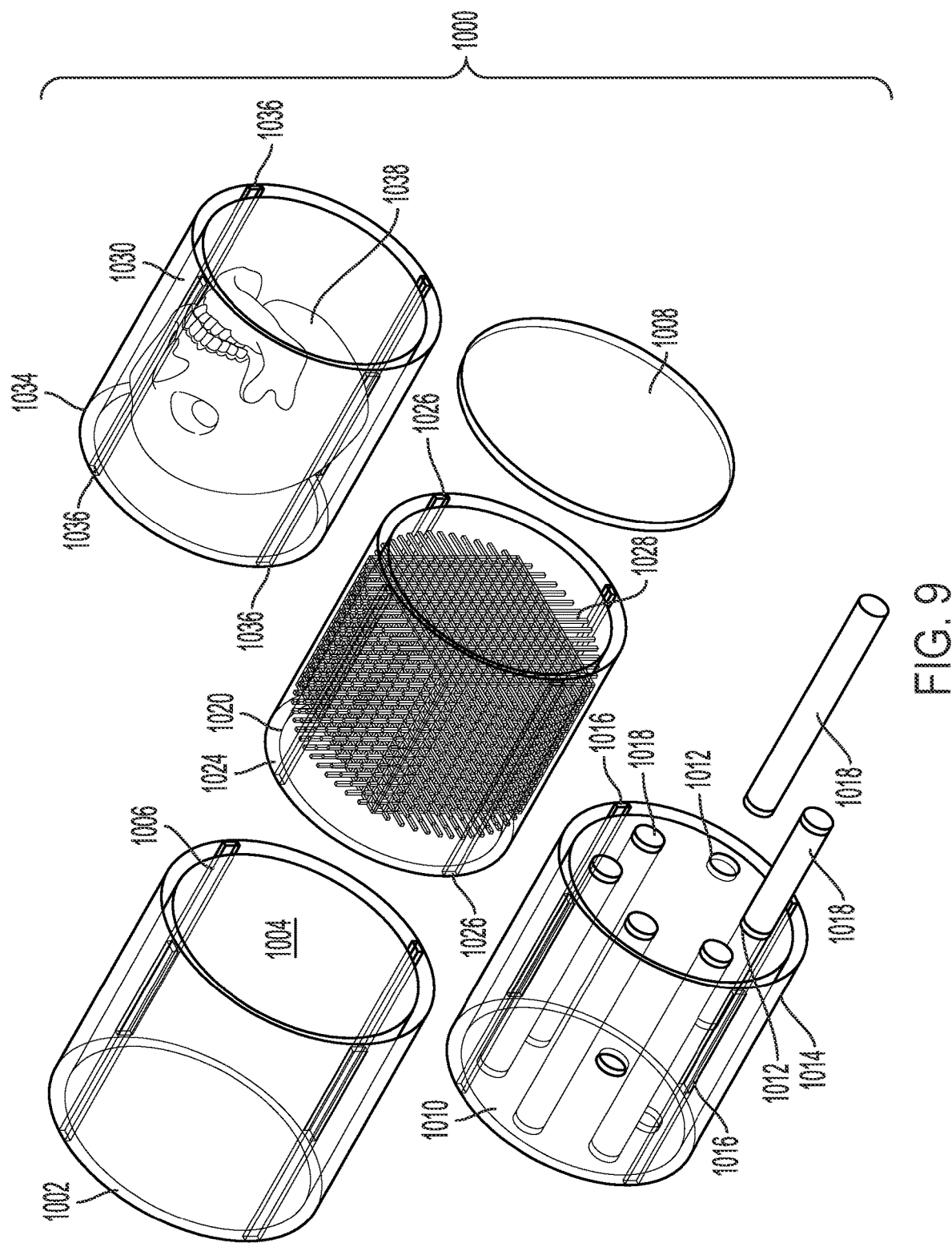
FIG. 9 depicts a magnetic resonance phantom kit with various components depicted as transparent for illustrative purposes, in accordance with at least one aspect of the present disclosure.

Referring primarily to FIG. 9, a MR phantom kit 1000 is shown. The MR phantom kit 1000 includes a plurality of components including a shell, or housing, 1002, multiple modular components 1010, 1020, 1030, and a lid 1008. Although only three modular components 1010, 1020, and 1030 are shown in FIG. 9, the reader will appreciate that the MR phantom kit is not limited to a kit having three modular components. The kit 1000 can include more than three modular components or less than three modular components.

Figure 10:
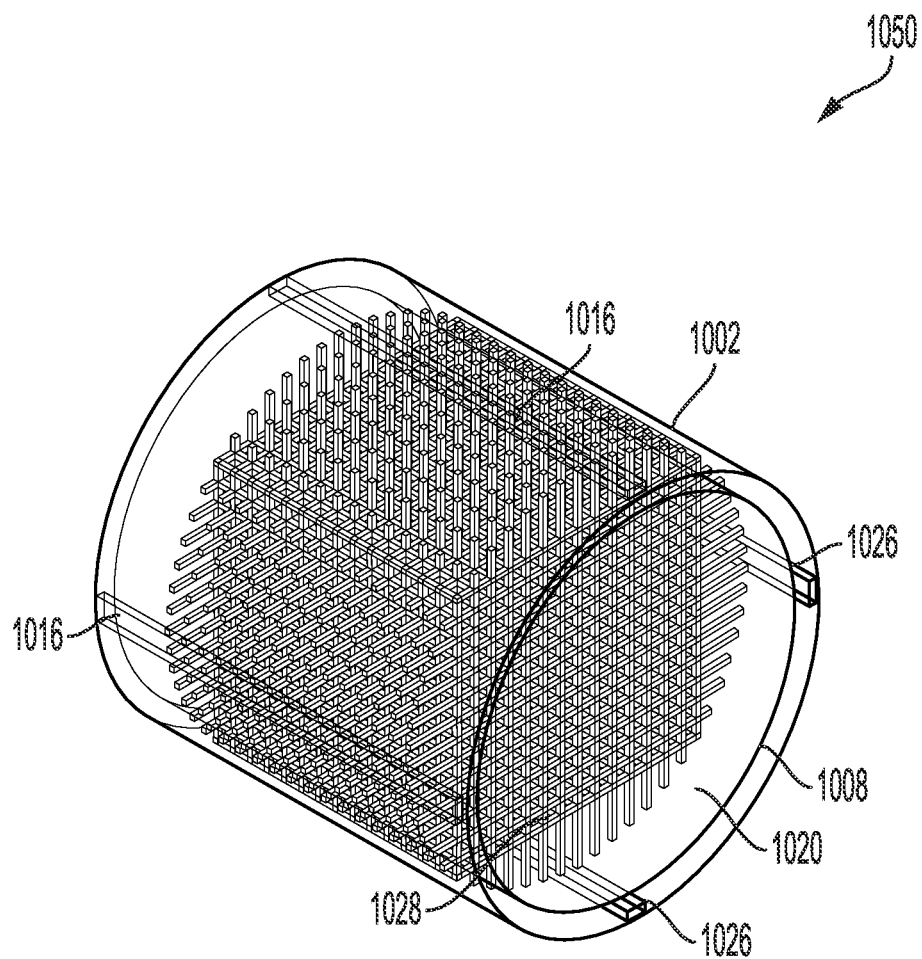
FIG. 10 depicts a magnetic resonance phantom assembled from the magnetic resonance phantom kit of FIG. 9 with various components depicted as transparent for illustrative purposes, in accordance with at least one aspect of the present disclosure.

The kit 1000 can be assembled into different configurations of a MR phantom. An exemplary configuration of an MR phantom 1050 is shown in FIG. 10. The various MRI systems disclosed herein, such as the MRI scanning system 100 (FIG. 1) and the MRI system 500 (FIG. 6), for example, can be utilized with the kit 1000 and phantom 1050 disclosed herein to obtain MR images thereof. The MRI scanning system 100 and MRI system 500 can also be used in connection with the alternative MR phantom kits and phantoms further described herein.

The shell 1002 defines a receptacle for receiving the modular components 1010, 1020, 1030 therein. The shell 1002 includes interlocking features 1006, which are defined on the inner surface 1004 of the shell 1002. The interlocking features 1006 define longitudinal recesses extending radially outward and structured to interlock with corresponding features (e.g. interlocking features 1016, 1026, 1036) on the modular components 1010, 1020, 1030. Four interlocking features 1006 are spaced apart around the perimeter of the shell 1002. Although four equally-spaced interlocking features 1006 are shown in FIG. 9, the reader will appreciate that a different number and/or arrangement of interlocking features 1006 can be utilized to releasably connect the modular component 1010 to the shell 1006.

The interlocking features 1006, 1016, 1026, 1036 define longitudinal features that can be slidably disposed to connect the components. Although the interlocking features 1006 are longitudinal recesses, in other instances, the interlocking features 1006 can define longitudinal slots dimensioned and positioned to be slidably received in longitudinal recesses in the modular components 1010, 1020, 1030. In still other instances, the interlocking features 1006, 1016, 1026, 1036 can comprise complementary pegs and receptacles, such as the interlocking features of LEGO® building bricks, for example.

The lid 1008 forms a cover for the shell 1002, such that modular components installed therein can be retained within the shell 1002. The lid 1008 can be snap-fit or friction-fit to the shell 1002 in various instances. In other instances, the lid 1008 can threadably engage the shell 1002. Additionally or alternatively, fasteners and/or clamps can releasably secure the lid 1008 to the shell 1002. The lid 1008 is configured to retain the modular component(s) 1010, 1020, and/or 1030 within the shell 1002.

In various instances, the shell 1002 and the lid 1008 can be comprised of plastic. Alternative materials are also contemplated.

In certain instances, the modular component(s) 1010, 1020 and/or 1030 can be releasably retained within the shell 1002 without the lid 1008 enclosing the shell 1002 such as with frictional forces alone, for example. In one aspect, the modular component(s) 1010, 1020, 1030 can releasably engage each other and/or the shell 1002, such as the interlocking features 1006 of the shell 1002, to secure the modular component(s) 1010, 1020, 1030 together and/or to the shell 1002.

In various instances, each modular component 1010, 1020, 1030 can be formed from a plastic body having different materials and/or structures interspersed therein.

The modular component 1010 depicted in FIG. 9 is a contrast insert, which is configured to receive at least one contrast medium therein. The modular component 1010 includes interlocking features 1016, which are defined in the outer surface 1014 thereof. The interlocking features 1016 are longitudinal ridges protruding radially outward. For example, the interlocking features 1016 can be dimensioned to fit into the longitudinal recesses of the interlocking features 1006. Four interlocking features 1016 are spaced apart around the perimeter of the modular component 1010. Although four equally-spaced interlocking features 1016 are shown in FIG. 9, the reader will appreciate that a different number and/or arrangement of interlocking features can be utilized to releasably connect the modular component 1010 to the shell 1006.

The modular component 1010 is configured to receive a contrast medium 1018 contained within tubular inserts. Different contrast mediums can be installed in the modular component 1010. For example, the contrast medium(s) 1018 can be selected based on the MRI system and/or desired characteristics of the MR image. The contrast medium 1018 is enclosed within tubular inserts that are configured to slide in and out of channels 1012 defined at least partially through the modular component 1010. In various instances, the contrast medium 1018 can be encapsulated within a vial or tube that is slidably retained in the modular component 1010. The tubes can be refillable in various instances.

Different tubes of contrast medium 1018 can be installed in the modular component 1010 and/or in different channels 1012 in the modular component 1010 to calibrate, test, evaluate and/or optimize different characteristics of various MRI systems and/or MRI operating parameters. For a first calibration, a first contrast medium 1018 can be utilized whereas a different contrast medium 1018 can be utilized for a second calibration. In various instances, different contrast mediums 1018 can be rearranged within the modular component 1010. For example, in some non-limiting aspects of the present disclosure, the spacing between contrast mediums 1018 can be adjusted between calibrations. In other non-limiting aspects, compartments within the modular component 1010 can be configured to open to receive the contrast medium 1018 therein. One or more of the compartments can be filled, emptied, and/or refilled with various different contrast materials depending on the desired characteristics of the test. For example, the contrast material can be nickel chloride, sodium chloride, copper sulfate, and/or gadolinium chloride.

Referring to FIG. 9, the contrast mediums 1018 extend longitudinally through the modular component 1010 in a radial array. Alternative configurations are contemplated. For example, the contrast mediums can be positioned in axial layers and/or stacks.

The modular component 1020 is a grid insert, which is configured to receive at least one grid 1028 therein. Grids can be configured to characterize geometric distortion in an image, for example. The modular component 1020 includes interlocking features 1026, which are defined in the outer surface 1024 thereof. The interlocking features 1026 are longitudinal ridges protruding radially outward. For example, the interlocking features 1026 can be dimensioned to fit into the longitudinal recesses of the interlocking features 1006. Four interlocking features 1026 are spaced apart around the perimeter of the modular component 1020. Although four equally-spaced interlocking features 1026 are shown in FIG. 9, the reader will appreciate that a different number and/or arrangement of interlocking features can be utilized to releasably connect the modular component 1020 to the shell 1002.

The grid 1028 is a three-dimensional grid. In other instances, multiple grids can be stacked and/or layered within the modular component 1020. The grids can be imaged in different slices of the MR image.

The modular component 1030 is an anatomical model insert, which is configured to receive at least one anatomical model 1038 therein. The modular component 1030 includes interlocking features 1036, which are defined in the outer surface 1034 thereof. The interlocking features 1036 are longitudinal ridges protruding radially outward. For example, the interlocking features 1036 can be dimensioned to fit into the longitudinal recesses of the interlocking features 1006. Four interlocking features 1036 are spaced apart around the perimeter of the modular component 1030.

Although four equally-spaced interlocking features 1036 are shown in FIG. 9, the reader will appreciate that a different number and/or arrangement of interlocking features can be utilized to releasably connect the modular component 1030 to the shell 1002.

The anatomical model 1038 is a three-dimensional model of a human head. In other instances, the anatomical model 1038 can be a different anatomical feature.

In various instances, the shell 1002 can be structured to receive more than one modular component 1010, 1020, 1030 therein. For example, multiple modular components can be installed and/or secured within the shell 1002 and/or to each other within the shell 1002. The modular components 1010, 1020, 1030 can be stacked and/or layered longitudinally and/or laterally within a shell and/or MR phantom assembly.

In still other instances, a MR phantom can be assembled without the shell 1002. For example, the modular components 1010, 1020, 1030 can directly engage and/or interlock together to form the MR phantom.

FIG. 10 depicts the MR phantom 1050 assembled from the MR phantom kit 1000. In the depicted configuration, the modular component 1020 is installed in the shell 1002 and the cover 1008 is secured to the shell 1002. In alternative configurations, the modular component 1010 or 1030 can be installed in the shell 1002. In still other instances, the modular component 1010 can be installed in the shell 1010; however, a different type and/or arrangement of contrast mediums 1018 can be installed in the modular component 1010. Additional configurations are also contemplated.

Figure 11:
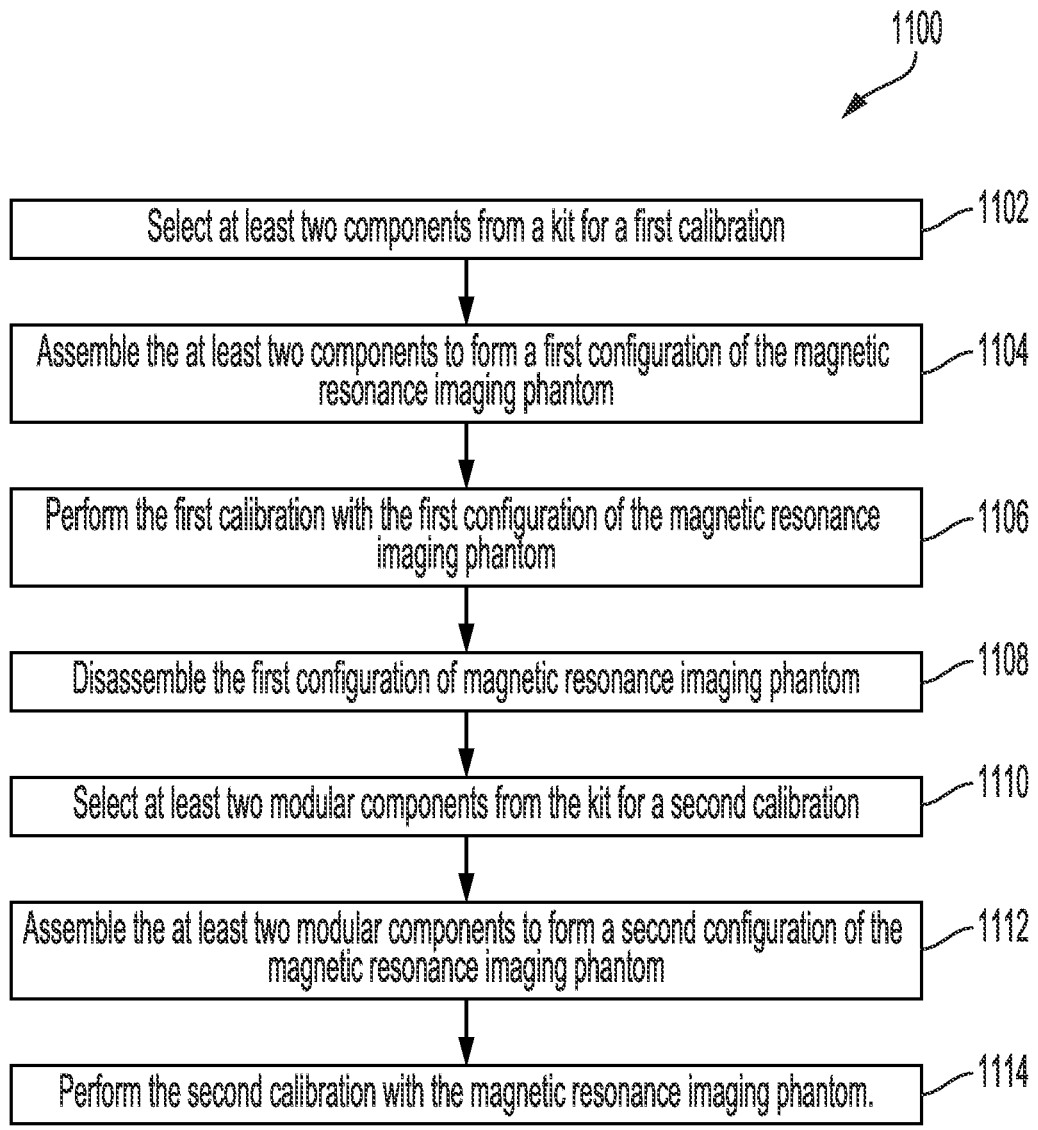
FIG. 11 is a flowchart depicting a method of using a magnetic resonance phantom kit, in accordance with at least one aspect of the present disclosure.

FIG. 11 is a flowchart 1100 depicting a method of using a MR phantom kit, such as the kit 1000 (FIG. 9), for example. To perform a first calibration, or test, at least two components from the magnetic resonance phantom kit can be selected (block 1102) and assembled together (block 1104) to form a first configuration of the MRI phantom. The components can include a shell, such as the shell 1002 (FIGS. 9 and 10) and at least one of the modular components 1010, 1020, 1030, for example. A first calibration can be performed by imaging the assembled MRI phantom (block 1106). For example, the MRI scanning system 100 (FIG. 1) and/or MRI system 500 (FIG. 6) can be used to image the assembled MRI phantom. The image can be analyzed for at least one characteristic and/or quality metric of the MRI system.

After the first calibration, the MRI phantom can be disassembled, or at least partially disassembled (block 1108). To perform a second calibration, or test, at least two components from the magnetic resonance phantom kit can be selected (block 1110) and assembled together (block 1112) to form a second configuration of an MRI phantom. The components can include a shell, such as the shell 1002 (FIGS. 9 and 10) and at least one of the modular components 1010, 1020, 1030, for example. In various instances, the same modular components can be assembled for the first configuration and the second configuration; however, the arrangement of the components, or at least a subset of the components, can be different. In other instances, the second configuration can include at least one different component than the first configuration. For example, interchangeable components can be exchanged between the first configuration and the second configuration. Additionally or alternatively, the MRI phantom can be scaled (e.g. extended or truncated). For example, additional modular components can be added. In other instances, at least one modular component can be removed.

A second calibration can be performed by imaging the reassembled MRI phantom (block 1114). For example, the MRI scanning system 100 (FIG. 1) and/or MRI system 500 (FIG. 6) can be used to image the assembled MRI phantom. The image can be analyzed for at least one characteristic and/or quality metric of the MRI system.

In various instances, the calibration steps comprise obtaining imaging data in a low-field strength primary magnetic field. In certain instances, the calibration steps comprise obtaining imaging data in an ultra-low field strength magnetic field.

In various instances, the different configurations of the MRI phantom can be selected and/or customized for different MRI systems. For example, different MRI systems can define different form factors and be configured for imaging structures of different sizes and/or different geometric constraints. As an example, MRI systems for imaging a patient's brain (e.g. during a neurosurgical intervention) can have a different form factor and/or different field of view than MRI systems for imaging a patient's neck, shoulder, heart, and/or lungs, for example.

In various instances, the different configurations of the MRI phantom can be selected and/or customized for different magnetic field strengths. For example, referring again to FIG. 9, the modular component 1010 can be configured such that each of the tubes of contrast medium 1018 are filled with solutions of contrast medium having different concentrations. A low-field MRI system can performing contrast imaging using the modular component 1010 having tubes of contrast medium 1018 filled with solutions of contrast medium having different concentrations.

In various instances, the different configurations can be selected for validation of different properties. In certain instances, the different configurations can be selected for validation of multiple properties.

In certain instances, the first configuration can be selected for validation of geometric distortion, contrast, structure, signal-to-noise, resolution, and intracranial vascular flow. In certain instances, the second configuration can be selected for validation of geometric distortion, contrast, structure, signal-to-noise, resolution, and intracranial vascular flow. In at least one instance, referring to FIG. 11 and also to FIG. 9, the at least two components of the first configuration or the second configuration can include the modular component 1010, and the corresponding first configuration or the second configuration can be used to validate contrast. In another instance, the at least two components of the first configuration or the second configuration can include the modular component 1020, and the corresponding first configuration or the second configuration can be used to validate geometric distortion. In yet another instance, the at least two components of the first configuration or the second configuration can include the modular component 1030, and the corresponding first configuration or the second configuration can be used to validate structural characteristics.

Referring again to FIG. 11, in various instances, at least one of the configurations is selected and/or customized for diffusion-weighted imaging. For example, in at least one instance, referring to FIG. 11 and also to FIG. 9, the at least two components of the first configuration or the second configuration can include the modular component 1010. Instead of the tubes the modular component 1010 being filled with contrast medium 1018, the tubes can be filled with solutions having different diffusion rates. The corresponding first configuration or second configuration including the modular component 1010 having tubes filled with solutions having different diffusion rates can be used for diffusion-weighted imaging.

Examples

Various additional aspects of the subject matter described herein are set out in the following numbered examples:

Example 1: A magnetic resonance imaging phantom kit, comprising: a plurality of modular components, wherein the plurality of modular components comprises: a first modular component; and a second modular component, wherein the second modular component is different than the first modular component; a shell structured to receive at least one modular component; and a lid attachable to the shell to enclose the at least one modular component received within the shell.

Example 2: The magnetic resonance imaging phantom kit of Example 1, wherein the first modular component and the second modular component are selected from a group consisting of a grid insert, a contrast insert, and an anatomical model insert.

Example 3: The magnetic resonance imaging phantom kit of any one of Examples 1 and 2, further comprising a plurality of contrast mediums, wherein the first modular component comprises a contrast insert structured to receive at least one contrast medium.

Example 4: A method of assembling a magnetic resonance imaging phantom, comprising: selecting at least two components from a kit for a first calibration; assembling the at least two components to form a first configuration of the magnetic resonance imaging phantom; performing the first calibration with the first configuration of the magnetic resonance imaging phantom; disassembling the first configuration of magnetic resonance imaging phantom; selecting at least two modular components from the kit for a second calibration; assembling the at least two modular components to form a second configuration of the magnetic resonance imaging phantom, wherein the second configuration is different than the first configuration; and performing the second calibration with the magnetic resonance imaging phantom.

Example 5: The method of Example 4, wherein performing the first calibration comprises obtaining imaging data in a low-field strength magnetic field.

Example 6: The method of any one of Examples 4 and 5, wherein the first configuration is customized for a first magnetic resonance imaging system, and wherein the second configuration is customized for a second magnetic resonance imaging system.

Example 7: The method of any one of Examples 4-6, wherein the first configuration is customized for a first magnetic field strength, and wherein the second configuration is customized for a second magnetic field strength.

Example 8: The method of any one of Examples 4-7, wherein the first configuration is selected for validation of two or more properties selected from a group consisting of geometric distortion, contrast, structure, signal-to-noise, resolution, and intracranial vascular flow.

Example 9: The method of any one of Examples 4-7, wherein the first configuration is customized for diffusion-weighted imaging.

Example 10: The method of any one of Examples 4-9, wherein the at least two components selected for the second calibration are different than the at least two components selected for the first calibration.

Example 11: The method of any one of Examples 4 and 5, wherein the at least two components selected for the second calibration are the same as the at least two components selected for the first calibration.

Example 12: A magnetic resonance imaging phantom kit, comprising: a shell comprising shell interlocking features; a first modular component, wherein the first modular component comprises first interlocking features configured to interlock with the shell interlocking features in different configurations; and a second modular component, wherein the second modular component is different than the first modular component, wherein the second modular component comprises second interlocking features configured to interlock with the shell interlocking features in different configurations, and wherein at least one of the first modular component and the second modular component comprises a contrast insert configured to receive a contrast medium.

Example 13: The magnetic resonance imaging phantom kit of Example 12, further comprising a third modular component comprising third interlocking features configured to interlock with the shell interlocking features in different configurations.

Example 14: The magnetic resonance imaging phantom kit of any one of Examples 12 and 13, wherein the contrast insert comprises a refillable tube.

Example 15: The magnetic resonance imaging phantom kit of any one of Examples 12-13, wherein the contrast medium is selected from a group consisting of nickel chloride, sodium chloride, copper sulfate, and gadolinium chloride.

Example 16: The magnetic resonance imaging phantom kit of any one of Examples 12 and 13, wherein the different configurations correspond to different magnetic field strength applications.

Example 17: The magnetic resonance imaging phantom kit of any one of Examples 12 and 13, wherein the different configurations correspond to different geometric form factors for different magnetic resonance systems.

Example 18: The magnetic resonance imaging phantom kit of any one of Examples 12 and 13 wherein the first modular component and the second modular component are selected for validation of two or more properties selected from a group consisting of geometric distortion, contrast, structure, signal-to-noise, resolution, and intracranial vascular flow.

Example 19: The magnetic resonance imaging phantom kit of any one of Examples 12 and 13, wherein the first modular component and the second modular component are selectively arranged for diffusion-weighted imaging.

Example 20: The magnetic resonance imaging phantom kit of any one of Examples 12-19, wherein the first modular component and the second modular component are selectively arranged for acquiring imaging data in low-field strength magnetic fields.

Though various aspects disclosed herein are directed to brain imaging and/or neurological interventions, the reader will appreciate that the various systems and methods disclosed herein can be used to image other portions of a patient's anatomy and/or different structures in various instances.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a control circuit computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A method of assembling a magnetic resonance imaging phantom, comprising:
    selecting at least two components from a kit for a first calibration;
    assembling the at least two components to form a first configuration of the magnetic resonance imaging phantom;
    performing the first calibration with the first configuration of the magnetic resonance imaging phantom;
    disassembling the first configuration of magnetic resonance imaging phantom;
    selecting at least two modular components from the kit for a second calibration;
    assembling the at least two modular components to form a second configuration of the magnetic resonance imaging phantom, wherein the second configuration is different than the first configuration; and
    performing the second calibration with the magnetic resonance imaging phantom.

2. A magnetic resonance imaging phantom kit, comprising:
    a shell comprising shell interlocking features;
    a first modular component, wherein the first modular component comprises first interlocking features configured to interlock with the shell interlocking features in different configurations; and
    a second modular component, wherein the second modular component is different than the first modular component, wherein the second modular component comprises second interlocking features configured to interlock with the shell interlocking features in different configurations, and wherein at least one of the first modular component and the second modular component comprises a contrast insert configured to receive a contrast medium, wherein the first modular component and the second modular component are selected for validation of two or more properties selected from a group consisting of geometric distortion, contrast, structure, signal-to-noise, resolution, and intracranial vascular flow.

3. A magnetic resonance imaging phantom kit, comprising:
    a shell comprising shell interlocking features;
    a first modular component, wherein the first modular component comprises first interlocking features configured to interlock with the shell interlocking features in different configurations; and
    a second modular component, wherein the second modular component is different than the first modular component, wherein the second modular component comprises second interlocking features configured to interlock with the shell interlocking features in different configurations, and wherein at least one of the first modular component and the second modular component comprises a contrast insert configured to receive a contrast medium, wherein the first modular component and the second modular component are selectively arranged for acquiring imaging data in low-field strength magnetic fields generated by a magnet assembly.

4. The method of claim 1, wherein performing the first calibration comprises obtaining imaging data in a low-field strength magnetic field.

5. The method of claim 1, wherein the first configuration is customized for a first magnetic resonance imaging system, and wherein the second configuration is customized for a second magnetic resonance imaging system.

6. The method of claim 1, wherein the first configuration is customized for a first magnetic field strength, and wherein the second configuration is customized for a second magnetic field strength.

7. The method of claim 1, wherein the first configuration is selected for validation of two or more properties selected from a group consisting of geometric distortion, contrast, structure, signal-to-noise, resolution, and intracranial vascular flow.

8. The method of claim 1, wherein the first configuration is customized for diffusion-weighted imaging.

9. The method of claim 1, wherein the at least two components selected for the second calibration are different than the at least two components selected for the first calibration.

10. The method of claim 1, wherein the at least two components selected for the second calibration are the same as the at least two components selected for the first calibration.

11. The magnetic resonance imaging phantom kit of claim 2, further comprising a third modular component comprising third interlocking features configured to interlock with the shell interlocking features in different configurations.

12. The magnetic resonance imaging phantom kit of claim 2, wherein the contrast insert comprises a refillable tube.

13. The magnetic resonance imaging phantom kit of claim 2, wherein the contrast medium is selected from a group consisting of nickel chloride, sodium chloride, copper sulfate, and gadolinium chloride.

14. The magnetic resonance imaging phantom kit of claim 2, wherein the different configurations correspond to different main magnetic field strength applications.

15. The magnetic resonance imaging phantom kit of claim 2, wherein the different configurations correspond to different geometric form factors for different magnetic resonance systems.

16. The magnetic resonance imaging phantom kit of claim 2, wherein the first modular component and the second modular component are selectively arranged for diffusion-weighted imaging.

17. The magnetic resonance imaging phantom kit of claim 2, wherein the first modular component and the second modular component are selectively arranged for acquiring imaging data in low-field strength magnetic fields generated by a magnet assembly.

* * * * *